United States Patent

Kny et al.

[11] 4,119,714
[45] Oct. 10, 1978

[54] GLYCERIN-ALKYLETHER-(1)-PHOSPHORIC ACID-(3)-MONOCHOLINE ESTERS AS ENHANCERS OF THE NATURAL RESISTANCE OF THE MAMMALIAN ORGANISM AGAINST NON-CARCINOGENIC PATHOGENS

[75] Inventors: Gunter Kny, Nassau, Lahn; Otto Westphal, Freiburg, both of Fed. Rep. of Germany

[73] Assignee: Max-Planck-Gesellschaft zur Förderung der Wissenschaften e. V., Göttingen, Fed. Rep. of Germany

[21] Appl. No.: 762,572

[22] Filed: Jan. 26, 1977

Related U.S. Application Data

[63] Continuation-in-part of Ser. No. 565,553, Apr. 7, 1975, abandoned, which is a continuation of Ser. No. 396,553, Sep. 12, 1973, abandoned, which is a continuation of Ser. No. 118,085, Feb. 23, 1971, abandoned.

[30] Foreign Application Priority Data

Feb. 27, 1970 [DE] Fed. Rep. of Germany ....... 2009342

[51] Int. Cl.² .................. A61K 31/685; A61K 31/66
[52] U.S. Cl. ..................................... 424/199; 424/211
[58] Field of Search ................................ 424/211, 199

[56] References Cited

PUBLICATIONS

Weltzien et al., Liebigs Ann. Chem., 709 (1967) pp. 234-239.

*Primary Examiner*—Jerome D. Goldberg
*Attorney, Agent, or Firm*—Hammond & Littell

[57] ABSTRACT

Pharmaceutical compositions comprising as the active ingredient an ether-lysolecithin of the formula

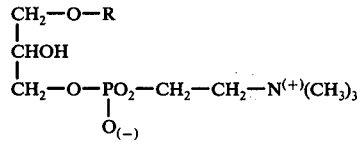

wherein R is alkyl of at least 12 and preferably 18 carbon atoms; the compositions are useful for enhancing the natural resistance of the mammalian organism against non-carcinogenic pathogens.

4 Claims, No Drawings

GLYCERIN-ALKYLETHER-(1)-PHOSPHORIC ACID-(3)-MONOCHOLINE ESTERS AS ENHANCERS OF THE NATURAL RESISTANCE OF THE MAMMALIAN ORGANISM AGAINST NON-CARCINOGENIC PATHOGENS

This is a continuation-in-part of copending application Ser. No. 565,553, filed Apr. 7, 1975, now abandoned; which in turn is a continuation of application Ser. No. 396,553, filed Sept. 12, 1973, now abandoned; which in turn is a continuation of application Ser. No. 118,085, filed Feb. 23, 1971, now abandoned.

This invention relates to novel pharmaceutical compositions comprising as the active ingredient an ether-lyso-lecithin, as well as to a method of enhancing the natural resistance of the mammalian organism against non-carcinogenic pathogens therewith.

More particularly, the present invention relates to the employment of glycerin-alkylether-(1)-phosphoric acid-(3)-monocholine esters, also referred to as ether-lysolecithins, of the formula

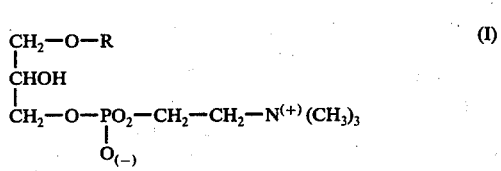

wherein R is alkyl of at least 12 and up to about 20 carbon atoms, but preferably of 18 carbon atoms, which are not metabolized by phospholipase B, as enhancers of the natural resistance of the warm-blooded animal organism against non-carcinogenic pathogens.

BACKGROUND OF THE INVENTION

The living cell, the smallest unit of living organism, has been studied to a very great extent. The morphological development of cells as well as, to a lesser degree, the essentials of the importance and functioning of the various subcellular structures are thoroughly understood. The cell membrane has also been the subject of exhaustive studies. As a result, subjects such as active and passive transport, inhibited or facilitated diffusion, countercurrent effects, pump effects, excitatory processes and the evalution impulses are all fairly well understood. It is thus very surprising that interfacial properties of membranes have been paid so little attention, although it is easy to see that many, if not the majority of membrane functions, are strongly influenced by membrane interfacial activity. The idea, that changing the interfacial activity might play a central role in central regulation and influencing mechanisms, is not so far-fetched, bearing in mind that changes in the activity of interfaces not only influence membrane permeability, but also the electrical potential thresholds which occur there. The fact that a desired activity may be brought about by influencing the activity of membrane interfaces is suggested by the following two factors: Firstly, the permeability of the membrane determines the direction amount and type of material to be transported through a membrane. Secondly, the membrane potential plays an important role in the transmission of impulses, a function that is regulated by changes in permeability.

However, influencing the interfacial activity by means of surfactant is frowned upon by most experts, as the surfactants are generally thought of as being highly toxic substances. This type of substance lowers the interfacial activity of the membrane to such an extent that its disruption is caused, at concentrations far lower than necessary for biological or pharmadynamic effects. Thus, surfactants are generally cytolytic in that they disrupt the membrane and destroy the cell. This cytolytic activity rises with increased surfactant absorption, in its accumulation in the membrane. Similarly, slow rates of metabolism also increase surfactant activity.

Lysolecithins, which are acyl-glyceral phosphorylcholine esters, are interfacially activity and are known to be cytolytic at high concentrations. In spite of this, the lethal dose of lysolecithins is relatively high, due to the fact that they are extremely rapidly metabolized by reacylation to lecithin or deacylation to glycerylphosphorylcholine.

THE INVENTION

We have made the surprising discovery that ether-lysolecithins of the formula I above, which are also surfactive but differ from lysolecithins in the replacement of the acyl group by an alkyl group, wherefor they should be non-metabolizable or at least considerably more difficultly metabolizable, are in fact also relatively non-toxic and also alter the interfacial activity of the cell membrane, so that they are useful as pharmacological agents for influencing and controlling the interfacial properties of cell membranes.

Thus, the practical utility of the ether-lysolecithins of the formula I, resides in their utilization as agents for increasing the natural resistance of the body, which manifests itself in an increased resistance to infections, as well as in a potentiation of the antigenicity of weaker, otherwise tolerated immunogens. Furthermore, the compounds of formula I can also be used as auxiliary agents in promotion of intercellular contact in vivo and are also useful in the isolation of cells capable of a high degree of immunity.

The preparation of compounds of the formula I is disclosed in the literature and can be carried out as described by D. Arnold, H. U. Weltzien and O. Westphal in Liebigs Ann. Chem. 709 (1967) 234. The synthesis proceeds as shown in the following schematic reaction sequence, starting with 1,3-benzylideneglycerin through glycerin-benzylether-(2), alkylation, reaction of the glycerin diether with phosphoric acid mono-2-bromoethylester-dichloride and introduction of the trimethylamine radical to glycerin alkylether-(1)-benzyl ether-(2)-phosphoric acid-choline ester, from which the protective benzyl group is then removed by hydrogenolysis.

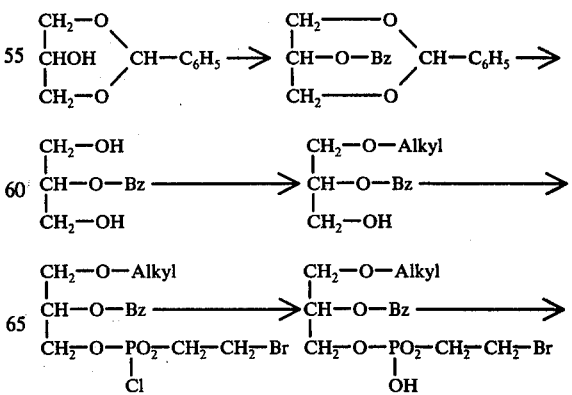

-continued

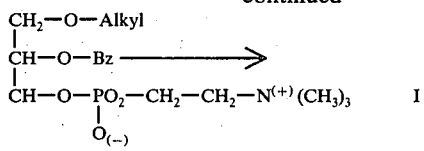

In this reaction sequence

Alkyl represents an alkyl radical of at least 12 carbon atoms and

Bz represents $-CH_2-C_6H_5$, i.e. the benzyl group.

The compounds of the formula I possess an asymmetric carbon atom and thus occur in two stereoisomeric forms. The preparation of the stereoisomeric compounds can be accomplished by suitable variation of the reaction scheme shown above, that is, by using optically active starting compounds or by subsequently dividing the racemic end product of the reaction into its optical antipodes.

The ether-lysolecithins embraced by formula I above, with the exception of the octadecylether, are known compounds, and the following example illustrates the preparation of the as yet unknown compound.

EXAMPLE 1

Glycerin-octadecylether-(1)-phosphoric acid-(3)-monocholine ester (a) Glycerin-octadecylether-(1)-benzylether-(2)

14 gm (0.07 mol) of glycerin-benzylether-(2) were dissolved in 500 ml of absolute xylene, 1.62 gm (0.07 mol) of sodium were added, and the mixture was gradually heated to 100° C. After 6 hours, by which time a thick sodium alcoholate-suspension had formed, 34 gm (0.09 mol) of n-octadecyl iodide were added, and the mixture was stirred for 6 hours more at 90° C. The solution first became clear but after some time sodium iodide gradually precipitated out. After cooling and adding 500 ml of water, the organic phase was separated and all of the components which are volatile at 0.1 mm Hg up to 180° C. were distilled off. The remaining 29.2 gm of raw product were chromatographed in three portions each on 120 gm of silicagel with ether/petroleum ether (1:1) as developing solvent. The yield of pure diether was 8.2 gm (19% of theory) as a colorless, wax-like substance. M.p. 45° C. ($R_f = 0.37$)

| Analysis: | $C_{28}H_{50}O_3$ | (mol. wt. 434.7) |
|---|---|---|
| Calculated: | C - 77.36%; | H - 11.59% |
| Found: | C - 77.03%; | H - 11.27% |

(b) Glycerin-octadecylether-(1)-benzylether-(2)-phosphoric acid-(3)-monocholine ester monohydrate 6.8 gm (0.016 mol) of glycerin-octadecylether-(1)-benzylether-(2) were dissolved in 60 ml of absolute chloroform, and the solution was slowly added dropwise at room temperature to a solution of 4 gm (0.017 mol) of phosphoric acid-mono-(2)-bromoethyl ester dichloride and 3.8 gm (0.065) mol) of triethylamine in 60 ml of chloroform. After standing at room temperature for 24 hours, the reddish-brown solution was hydrolyzed by vigorously stirring it for 2 hours with 8 ml of water. After evaporation in vacuo, the residue was dried over phosphorus pentoxide in a high vacuum and then extracted with 300 ml of absolute petroleum ether (boiling point range 60°-70° C.). The undissolved ammonium salts were vacuum-filtered off, and the filtrate was evaporated to dryness. The residue was then dissolved in 100 ml of chloroform, and the solution was shaken vigorously for 5 minutes with 20 ml of saturated aqueous barium acetate. The barium salt was purified by chromatography on 200 gm of silicagel, using chloroform/methanol (9:2) as the flow agent. The main product was obtained as a colorless rubbery substance ($R_f = 0.58$). After reprecipitation from absolute ether with absolute acetone 6.2 gm of the pure barium salt were obtained. This salt was then shaken in 150 ml of absolute methanol (heated to 50°-60° C.) with 10 ml of air-dried cation exchange resin (H-form) for 15 minutes, whereby everything gradually went into solution. After vacuum filtration and evaporation of the solvent, 5.8 gm of free bromoethylphosphate were obtained as a colorless oil. This oil was then refluxed with 300 ml of a methanolic 12.5% solution of trimethylamine for 6 hours. The solid lecithin bromide (7.0 gm) obtained after evaporation was stirred vigorously in 200 ml of methanol with 2.8 gm of silver acetate for 30 minutes at room temperature, whereby a wax-like raw lecithin was formed, from which the last traces of silver acetate were removed by chromatography on 200 gm of silicagel, using chloroform/methanol/water (65:25:4) as solvent system ($R_f$ value = 0.3). After reprecipitation from a small amount of chloroform with acetone, the pure product was obtained in the form of a colorless powder with an overall yield of 40% of theory.

| Analysis: | $C_{33}H_{64}O_7NP$ | (mol. wt. 617.9) | (monohydrate) | |
|---|---|---|---|---|
| Calculated: | C - 64.15%; | H - 10.44%; | N - 2.27%; | P - 5.01% |
| Found: | C - 63.40%; | H - 10.26%; | N - 2.32%; | P - 5.07% |

(c) Glycerin-Octadecylether-(1)-phosphoric acid-(3)-monocholine ester monohydrate 1.0 gm (1.62 millimol) of glycerin-octadecylether-(1)-benzylether-(2)-phosphoric acid-(3)-monocholine ester was hydrogenated with 250 mgm of palladized charcoal in 150 ml of absolute methanol for 7 hours at 40° C. and normal pressure. Subsequent chromatography of the hydrogenation product on 100 gm of silicagel with chloroform/methanol/water (65:24:4) yielded the pure ether-lysolecithin as a colorless powder ($R_f$-value = 0.2). The yield was 0.64 gm, which corresponded to 75% of theory.

| Analysis: | $C_{26}H_{58}O_7NP$ | (mol. wt. 527.7) | (monohydrate) | |
|---|---|---|---|---|
| Calculated: | C - 59.17%; | H - 11.08%; | N - 2.65%; | P - 5.87% |
| Found: | C - 57.69%; | H - 11.26%; | N - 2.48%; | P - 5.60% |

The enhancing effect upon the resistance to infections was tested by determination of survival time of mice after infection with non-carcenogenic pathogenic germs analogous to the test method of H. G. Howard, D. R. Rowly and A. C. Wardlaw, Nature 179 (1957) 317. Animals, treated by i.p. infection of etherlysolecithins of the formula I prior to i.p. infection with *E. coli* 145, showed a three times longer survival time than the untreated controls. The reason for this increased resistance can be regarded in terms of increased phagocytosis activity. Animals pretreated with ether-lysolecithins of the formula I showed an increased absorption of germs in the phagocytic cytoplasma (macro- and microphages). Both the number of cells capable of phagocytosis and also the number of bacteria absorbed per cell increased severalfold. These results were obtained by both in vivo and in vitro experiments.

The compounds of the formula I also exhibit immunologic adjuvant activities, which is also considered to be a form of enhancement of the natural resistance of the warm-blooded animal organism.

In immunology, adjuvants are understood to be substances which, when mixed with an antigen, enhance antigenicity and increase the immune response of the organism to an antigenic stimulus, i.e. the formation of antibodies. With the aid of adjuvants it is, for instance, possible to counteract the so-called immunoparalysis, that is, to initiate the formation of antibodies even with those antigens which are otherwise tolerated by the organism.

The immunologic adjuvant activity of the compounds of the formula I was ascertained as follows:

(1) The test was carried out in analogy to the method of Dresser [Immunology 9 (1965) 261]. The basic principle of this test procedure consists in the inducement of tolerance by means of a soluble protein. This test procedure determines the ability of substances to increase the immune response in the organism against the extremely weak immunogenic bovine gammaglobulin (BGG) to the degree that antibodies for this protein may be clearly proven. For this purpose, mice are administered a 5 mgm dose of centrifuged, aggregate-free BGG by intraperitoneal injection. Normally, with this dose no antibodies are detectable after 8 to 10 days, which means that the animals are not immunized, and under these conditions they are incapable of an immune response to BGG. However, administration of BGG in combination with an immunologic adjuvant prevents the temporary development of tolerance, and the animals then form antibodies against BGG which they normally tolerate. Some 10 to 12 days following initial administration of the tolerific protein, BGG labeled with iodine-125 is again injected. If the animals are tolerant, the labeled antigen is slowly broken down similar to endogenous gammaglobulin. On the other hand, if the animals are immune a so-called immune elimination takes place, i.e. the labeled antigen is removed from the circulation at a much more rapid rate. Thus, the speed of elimination of iodine-125-labeled BGG is a measure of antibodies formation.

In tests with the compounds of the instant invention it was found that animals treated with labeled BGG and a compound of the formula I eliminated the tracer protein from the circulation about 10 to 100 times faster than saline-treated controls.

(2) Another immunologic test method for antibodies by which immunologic adjuvant properties can be determined is based on the principle that the immunogen (BGG) is coupled with erythrocytes, and the thus treated cells are incubated for 20 hours at 4° C. with serum in a geometric series of dilution. If the serum contains antibodies, the erythrocyte agglutinates. The highest concentration at which this phenomenon can still be observed is known as the antibodytiter of the serum.

This considerably less accurate method, however, also clearly proved that the compounds of the formula I are highly active immunologic adjuvants.

For pharmaceutical purposes the compounds of the formula I are administered to warm-blooded animals perorally or parenterally, but preferably by intraperitoneal injection, as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspension, emulsions, syrups, suppositories and the like. One effective dosage unit of the compounds of the formula I is from 0.5 to 10 mgm/kg body weight, depending upon the degree of potentiation of natural resistance desired.

The following examples illustrate a few dosage unit compositions comprising a compound of the formula I as an active ingredient and represent the best modes contemplated of putting the invention into practical use. The parts are parts by weight unless otherwise specified.

EXAMPLE 2

Coated Pills

The pill core composition is compounded from the following ingredients:

| | |
|---|---|
| Glycerin-octadecylether-(1)-phosphoric acid-(3)-monocholine ester monohydrate | 100.0 parts |
| Secondary calcium phosphate, anhydrous | 73.0 parts |
| Corn starch | 55.0 parts |
| Polyvinylpyrrolidone | 5.0 parts |
| Carboxymethyl cellulose | 5.0 parts |
| Magnesium stearate | 2.0 parts |
| Total | 240.0 parts |

Preparation

The monocholine phosphate is intimately admixed with calcium phosphate and the corn starch, the resulting mixture is moistened with an ethanolic 10% solution of the polyvinylpyrrolidone, the moist mass is forced through a 1.5 mm-mesh screen, the resulting granulate is dried at 45° C. and again passed through the screen, the dry granulate is uniformly admixed with the carboxymethyl cellulose and the magnesium stearate, and the finished composition is compressed into 240 mgm-pill cores which are subsequently coated with a thin shell consisting essentially of a mixture of talcum and sugar. Each coated pill contains 100 mgm of the monocholine phosphate and is an oral dosage unit composition which effectively increases the natural resistance of the warm-blooded animal organism against non-carcinogenic pathogens.

EXAMPLE 3

Tablets

The tablet composition is compounded from the following ingredients:

| | |
|---|---|
| Glycerin-dodecylether-(1)-phosphoric acid-(3)-monocholine ester monohydrate | 200.0 parts |
| Lactose | 100.0 parts |
| Corn starch | 80.0 parts |
| Polyvinylpyrrolidone | 12.0 parts |
| Cellulose, microcrystalline | 54.0 parts |
| Magnesium stearate | 4.0 parts |
| Total | 450.0 parts |

Preparation

The monocholine phosphate is intimately admixed with the lactose, the corn starch and the polyvinylpyrrolidone, the mixture is moistened with water; the moist mass is forced through a 1.5 mm-mesh screen, dried at 45° C. and again passed through the screen; the resulting dry granulate is uniformly admixed with the cellulose and the magnesium stearate, and the finished composition is compressed into 450 mgm-tablets. Each tablet contains 200 mgm of the monocholine phosphate and is an oral dosage unit composition which effectively increases the natural resistance of the warm-blooded animal organism against non-carcinogenic pathogens.

EXAMPLE 4

Drop Solution

The solution is compounded from the following ingredients:

| | | |
|---|---|---|
| Glycerin-hexadecylether-(1)-phosphoric acid-(3)-monocholine ester monohydrate | 1.0 | parts |
| Methyl p-hydroxybenzoate | 0.035 | parts |
| Propyl p-hydroxybenzoate | 0.015 | parts |
| Propyleneglycol | 45.0 | parts |
| Oil of anise | 0..05 | parts |
| Menthol | 0.05 | parts |
| Saccharin sodium | 1.0 | parts |
| Ethanol | 1.0 | parts |
| Distilled water q.s.ad | 100.0 | parts by vol. |

Preparation

The propyleneglycol is admixed with 45 parts of distilled water, and the monocholine phosphate is dissolved in the mixture (solution A). The p-hydroxybenzoates, the menthol and the oil of anise are dissolved in the ethanol (solution B). Solutions A and B are admixed, the saccharin sodium is added, and the resulting solution is diluted with distilled water to the indicated volume and filtered. 1 ml of the filtrate (about 20 drops) contains 10 mgm of the monocholine phosphate and is an oral dosage unit composition which effectively increases the natural resistance of the warm-blooded animal organism against non-carcinogenic pathogens.

EXAMPLE 5

Hypodermic Solution

The solution is compounded from the following ingredients:

| | | |
|---|---|---|
| Glycerin-octadecylether-(1)-phosphoric acid-(3)-monocholine ester monohydrate | 50.0 | parts |
| Polypropyleneglycol | 2500.0 | parts |
| Tartaric acid | 15.0 | parts |
| Distilled water q.s.ad | 5000.0 | parts by vol. |

Preparation 2000 parts of distilled water are heated to about 50° C., and then the indicated amount of polypropyleneglycol is added thereto; thereafter, the monocholine phosphate and the tartaric acid are dissolved therein, and the resulting solution is diluted with additional distilled water to the indicated volume. The finished solution is filtered until free from suspended particles, and the filtrate is filled into 5 ml-ampules which are then sealed and sterilized. Each ampule contains 50 mgm of the monocholine phosphate, and the contents thereof are an intraperitoneally injectable dosage unit composition which effectively increases the natural resistance of the warm-blooded animal organism against non-carcinogenic pathogens.

Analogous results are obtained when any one of the other ether-lysolecithins embraced by formula I is substituted for the particular ether-lysolecithin in Examples 2 through 5. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of increasing the immune response of the organism of a warm-blooded animal to a non-carcinogenic, antigenic stimulus, which comprises administering to said animal an effective immune response increasing amount of a compound of the formula

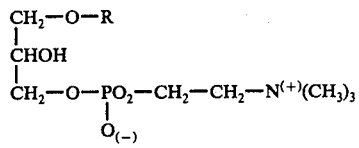

wherein R is alkyl of 12 to about 20 carbon atoms.

2. The method of claim 1, where said compound is glycerin-octadecylether-(1)-phosphoric acid-(3)-monocholine ester.

3. The method of claim 1, where said compound is glycerin-dodecylether-(1)-phosphoric acid-(3)-monocholine ester.

4. The method of claim 1, where said compound is glycerin-hexadecylether-(1)-phosphoric acid-(3)-monocholine ester.

* * * * *